United States Patent [19]

Lehner et al.

[11] Patent Number: 5,941,814
[45] Date of Patent: Aug. 24, 1999

[54] ARRANGEMENT FOR ADJUSTING AND FIXING THE RELATIVE POSITION OF TWO COMPONENTS OF AN ACTIVE OR PASSIVE HEARING IMPLANT

[75] Inventors: Rolf Lehner, Esslingen; Hans Leysieffer, Taufkirchen, both of Germany

[73] Assignee: Implex Aktiengesellschaft Hearing Technology, Ismaning, Germany

[21] Appl. No.: 09/042,805

[22] Filed: Mar. 17, 1998

[30] Foreign Application Priority Data

Sep. 3, 1997 [DE] Germany .................. 197 38 587

[51] Int. Cl.$^6$ ................................... H04R 25/00
[52] U.S. Cl. .............................................. 600/25
[58] Field of Search ................... 600/25, 559; 381/60, 381/312, 151

[56] References Cited

U.S. PATENT DOCUMENTS 3,196,462  7/1965  Robinson .
3,931,648  1/1976  Shea, Jr. .
4,655,776  4/1987  Lesinski .
5,370,689  12/1994  Causse .
5,433,749  7/1995  Clifford et al. .
5,771,298  6/1998  Davis et al. ............................. 381/60
5,772,575  6/1998  Lesinski et al. ......................... 600/25
5,833,626  11/1998  Leysieffer ............................... 600/559

Primary Examiner—George Manuel
Attorney, Agent, or Firm—Sixbey, Friedman, Leedom & Ferguson; David S. Safran

[57] ABSTRACT

Arrangement for adjusting and fixing the relative position of two components of an active or passive hearing implant. A first one of the elements is rod-shaped at least in the fixing region. The other of the elements, at least in the fixing region, is sleeve-shaped and can be plastically cold-deformed by a crimping tool or is made as a belt loop which can be tightened and in the fixed state loops around the rod-shaped part over an angle of at least 360°. The two elements are joined permanently to one another without play by cold-flow deformation of the sleeve-shaped part or by force-fit and/or form fit when the belt loop is tightened.

33 Claims, 7 Drawing Sheets

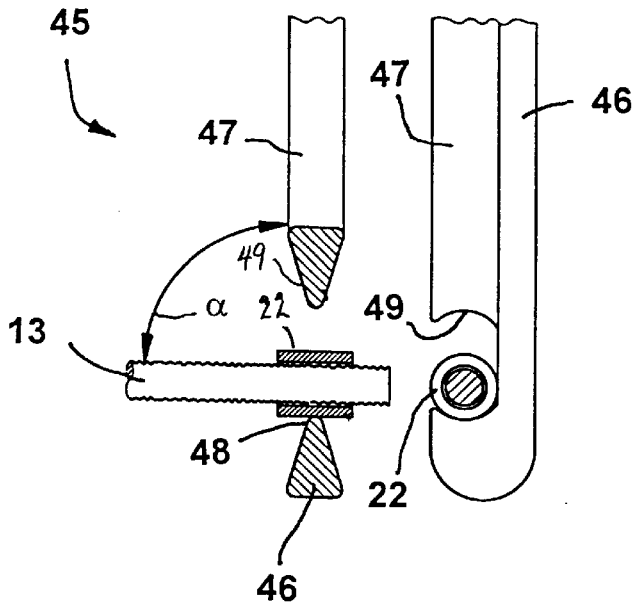
Fig. 13a
Fig. 13b
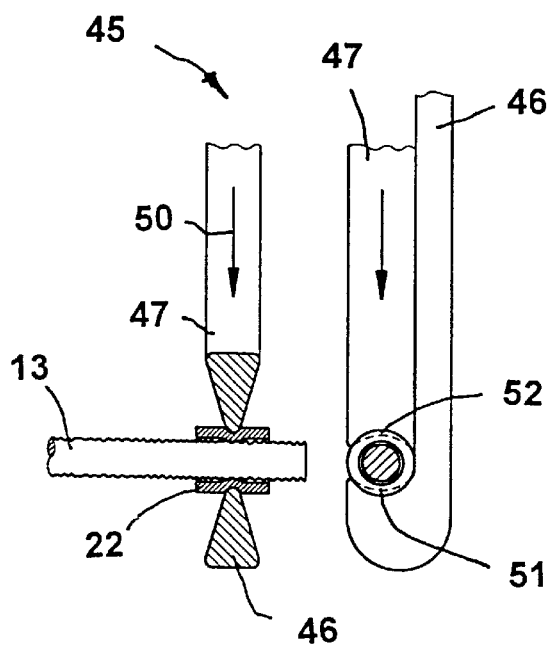
Fig. 14a
Fig. 14b
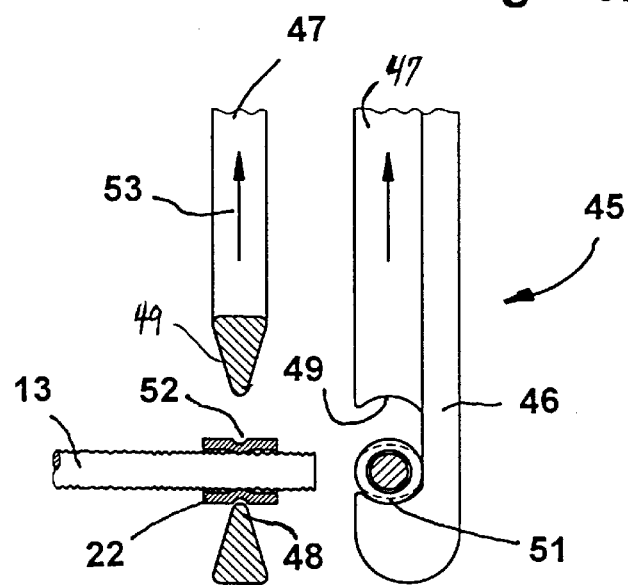
Fig. 15a
Fig. 15b

ARRANGEMENT FOR ADJUSTING AND FIXING THE RELATIVE POSITION OF TWO COMPONENTS OF AN ACTIVE OR PASSIVE HEARING IMPLANT

BACKGROUND OF THE INVENTION

1. Field of the Invention

The invention relates to an arrangement for adjusting the relative position of two components of an active or passive hearing implant and for fixing these elements in the relative position to which they have been adjusted.

2. Description of Related Art

Commonly owned, U.S. Pat. No. 5,277,694 discloses an electromechanical transducer for implantable hearing aids for direct mechanical excitation of the middle or inner ear, in which one wall of a hermetically sealed and biocompatible housing is made as an oscillatory membrane which, with a piezoelectric ceramic disk applied to the inside, represents an electromechanically active heteromorphic composite element, and whose mechanical vibrations are transmitted via a mechanically stiff coupling rod fixedly securely on the outside of the membrane and a mechanically stiff coupling element to the middle ear ossicle or directly to the inner ear.

In the known arrangement, the coupling element is made on the end to be joined to the coupling rod as a belt loop which is inserted into a bulge of the coupling rod, and which, in the fixed state, loops the bulged part of the coupling rod on part of its periphery. Fixing takes place by pressing the belt loop closed or by application of a drop of adhesive. The mutual position of the coupling rod and coupling element in the axial direction of the coupling rod is strictly dictated by the bulge of the coupling rod, the bulge contributing to keeping the coupling element in the prescribed position with reference to the coupling rod. Likewise, the long term stability of the connection of the coupling rod and coupling elements may leave something to be desired.

SUMMARY OF THE INVENTION

The primary object of the present invention is to devise an arrangement which makes it possible to adjust the relative position of the two elements of an active or passive hearing implant easily in situ at the implantation site and to reliably fix the elements in the relative position to which they have been adjusted with long term stability.

This object is achieved in accordance with the invention by an arrangement for adjusting and fixing the relative position of two elements of an active or passive hearing implant in which one of the elements to be fixed, at least in the fixing region, being made sleeve-shaped and being plastically cold-deformable by means of a crimping tool, the other element being made rod-shaped, at least in the fixing region, and be provided with a rough surface which has not been plastically cold-deformable under the influence of the crimping force applied by means of a crimping tool, and in the fixed state the sleeve-shaped part of one element being attached by being deformed by cold flow by the crimping force on the rod-shaped part of the other element without play and permanently.

The arrangement of the invention does not require a fixing aid according to the coupling rod-bulge type of known approach. The rod-shaped part can rather be easily made straight, so that in the course of implantation, high flexibility for in situ adjustment of the relative position of the two elements is ensured, not only in the peripheral direction, but also in the axial direction of the rod-shaped part. The cold-flow deformation of the sleeve-shaped part causes mutual clutching of the two parts on the rough rod-shaped part; this is itself able to transfer forces in the axial direction which are orders of magnitude higher than the necessary stimulation forces. This should be attributed especially to the fact that the transfer of axial force amounts to the sum of the microdenticulations between the rough surface of the rod-shaped part and the material of the sleeve-shaped component deformed by cold flow and to an additional portion of frictional force between the two parts. The arrangement of the invention allows the sleeve-shaped part to be first loosely placed on the rod-shaped part during the operation, and then, the two parts to be moved into the proper relative position, followed by crimping in situ in the middle ear.

According to one version of the invention, the arrangement for adjusting the relative position of two elements of an active or passive hearing implant and for fixing these elements in the relative position to which they have been adjusted can also be structured such that one of the elements, at least in the fixing area, is made as a belt loop which can be tightened, that the other element, at least in the fixing area, is made in the shape of a straight rod, and that in the fixed state, the loop-shaped part of one element surrounds the straight rod-shaped part of the other element over an angle of at least 360° and is attached permanently and without play by force-fit and/or form-fit on the rod-shaped part of the other element.

Other preferred embodiments of the invention are also possible. In particular, one of the two elements can be a coupling rod which is joined with an actively oscillatory part of an implantable hearing aid transducer, while the other of the two elements is a coupling element which can be coupled to the ossicular chain or perilymph. The implant can also be made as a total or partial replacement of the ossicular chain.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIGS. 13a & 13b, 14a & 14b and 15a & 15b schematically depict a crimping process and the crimping tool used for this purpose, the "a" views being in a direction which is at a right angle to the viewing direction of the "b" views;

DETAILED DESCRIPTION OF THE PREFERRED EMBODIMENTS

Figure 1:
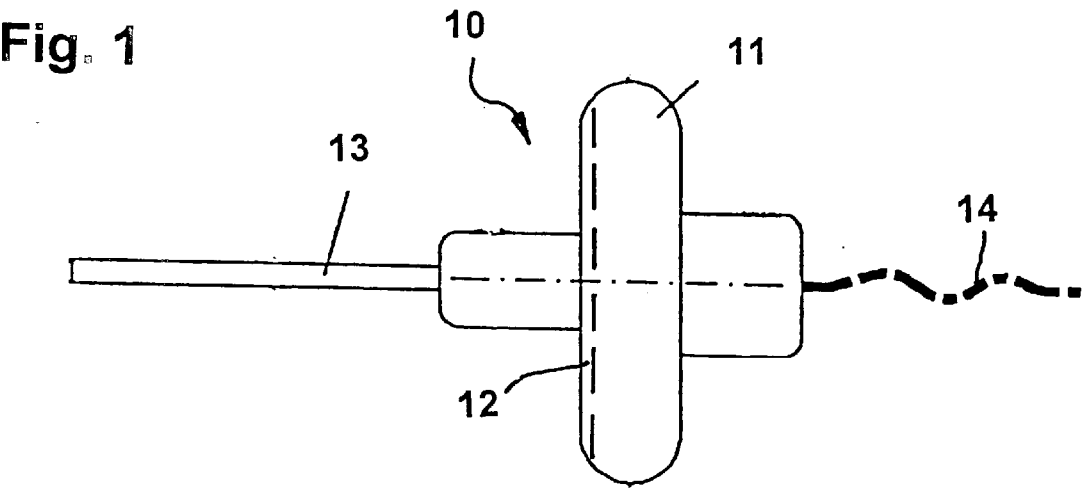
FIG. 1 is an enlarged schematic depiction of a hearing aid transducer with a coupling rod.

In FIG. 1, an implantable hearing aid transducer 10 is shown which can be made, for example, as a piezotransducer vibratory stimulation of the ossicular chain. The hearing aid transducer 10 has a biocompatible housing 11 which is hermetically sealed on all sides, and it can be equipped with an electromechanically active heteromorphic composite element of the type known from the initially mentioned U.S. Pat. No. 5,277,694

A coupling rod 13 is mechanically securely joined to an active vibratory part 12 of the hearing aid converter 10, which is shown only schematically in FIG. 1. In the illustrated embodiment coupling rod 13 over its entire length essentially has the shape of a straight cylinder. If an electrical voltage is applied to the cable connection 14 of the hearing aid transducer 10, the coupling rod 13 is forced to execute vibratory oscillations in the axial direction of the coupling rod by means of the active vibratory part 12. Consequently, audio signals which are picked up by a microphone (not shown) are electrically converted, and after electronic amplification in an electronic module of the hearing aid, lead directly to mechanical displacements of coupling rod 13. These displacements correspond to acoustic information. Displacements of coupling rod 13 are relayed to the ossicular chain of the middle ear or to the stapes or the oval or round window, or also an artificial window, by mechanical coupling elements which can be fixedly securely on coupling rod 13. When the preprocessing electronic system is designed accordingly, they cause an audiologic amplification effect.

Figure 2:
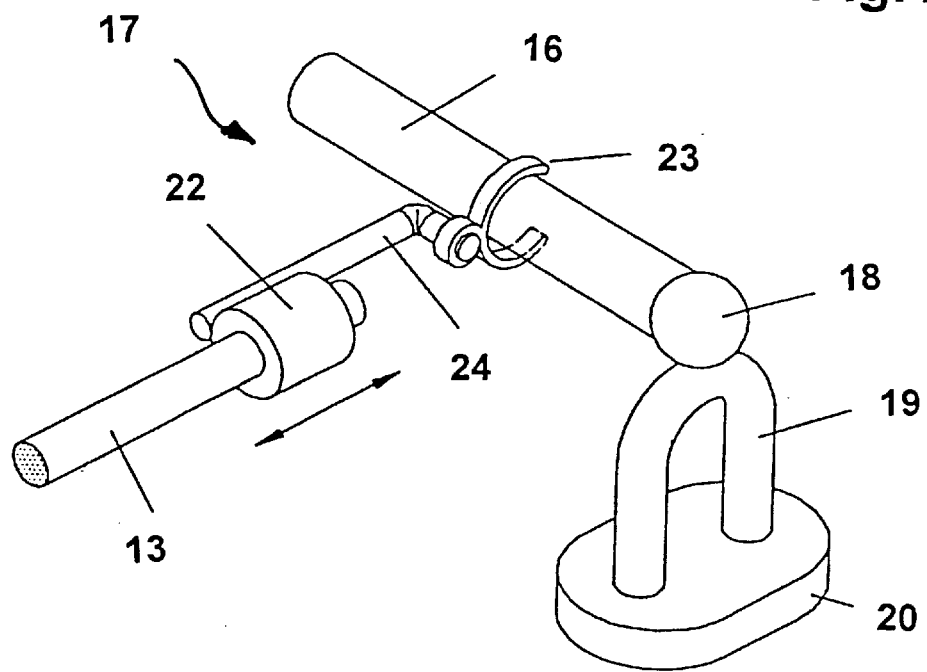
FIG. 2 shows, on an even larger scale, a perspective view of a coupling element joined to the coupling rod of the hearing aid transducer of FIG. 1 for coupling of the hearing aid transducer to the long incus process.
Figure 3:
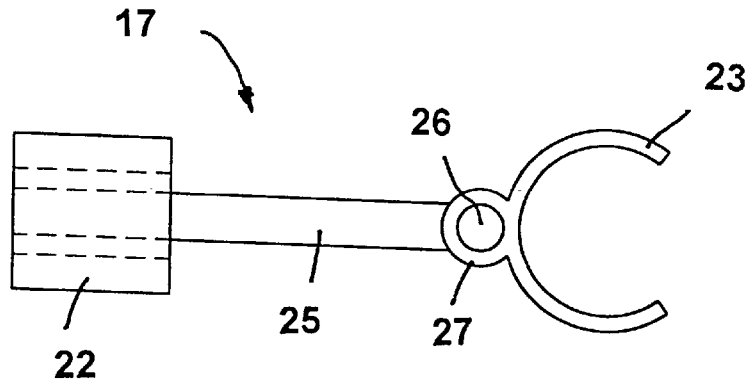
FIG. 3 is a side view of the coupling element of FIG. 2.
Figure 4:
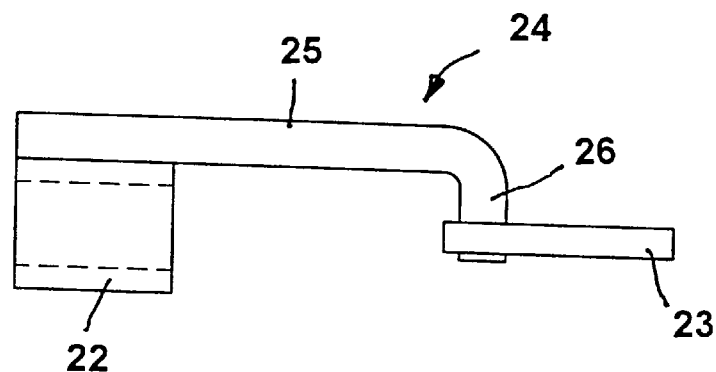
FIG. 4 is a top view of the coupling element of FIG. 2.
Figure 5:
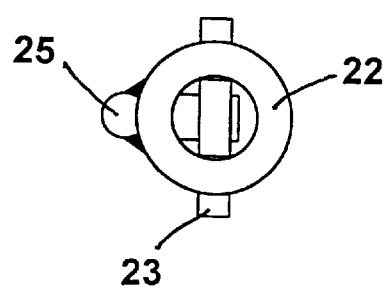
FIG. 5 is back view of the coupling element of FIG. 2.

FIG. 2 shows a coupling element 17 designed for connection of the coupling rod 13 to the long incus process 16. This coupling is suitable when the ossicular chain is intact. Here, in FIG. 2, the incudostapedial joint 18, stapes superstructure 19 and stapes footplate 20 are shown schematically. Coupling element 17 has a crimp sleeve 22, C-shaped coupling part 23, and a middle part 24 which provides for a secure mutual connection of the crimp sleeve 22 and coupling part 23. The coupling element 17 is illustrated in FIGS. 3, 4 and 5 on a further enlarged scale. As shown there, the middle part 24 is formed of a bent wire piece, one arm 25 of which is longitudinally extended and is joined to the outside of crimp sleeve 22, for example, soldered or welded. The free end of the other, short arm 26 of the middle part 24 fits into the eye 27 formed on the coupling part 23, where it is attached, for example, by welding or soldering. In the mounted state, the C-shaped coupling part 23 surrounds the long incus process 16 (FIG. 2). The C-shaped coupling part 23 can be wire-eroded especially from pure titanium foil (purity >99.6%) with a thickness on the order of 200 microns.

Figure 6:
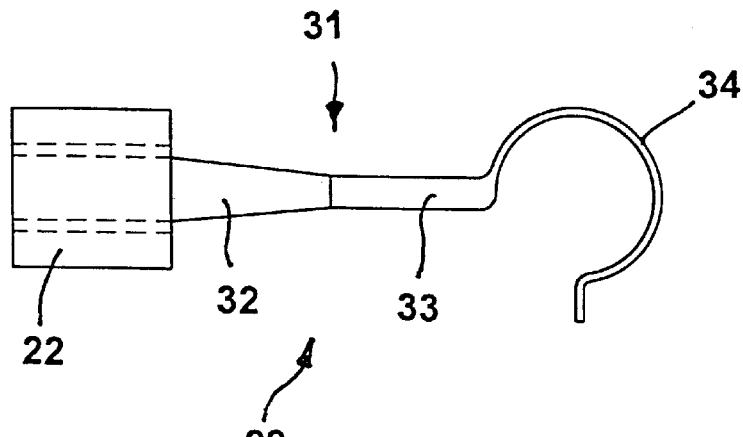
FIGS. 6, 7 and 8 are, respectively, a side view, a top view, and back view of a coupling element according to a modified embodiment.
Figure 7:
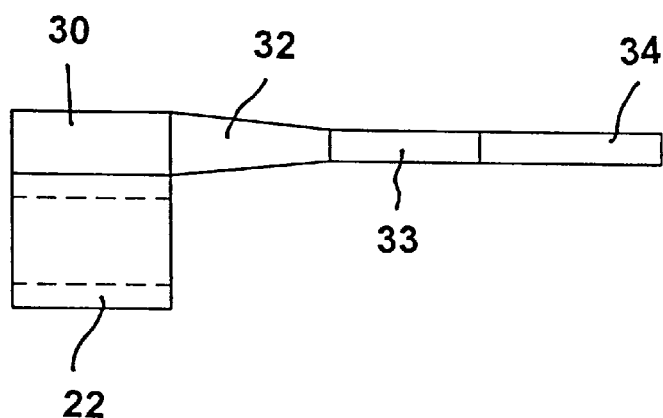
Figure 8:
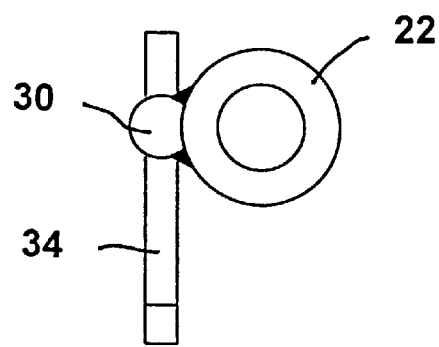

FIGS. 6–8 show a coupling element 29 according to a modified embodiment that is, likewise, especially suitable for coupling to the long incus process 16. Here, the crimp sleeve 22 is securely joined (for example, by a weld or solder connection) to a first cylindrical section 30 of the middle part 31. The cylindrical section 30 is adjoined by a conically tapering section 32 which passes into a second cylindrical section 33 that has a diameter which is less than that of section 30. Cylindrical section 33 is integrally joined to a belt loop 34 which can, for example, be placed around the long incus process 16.

Figure 9:
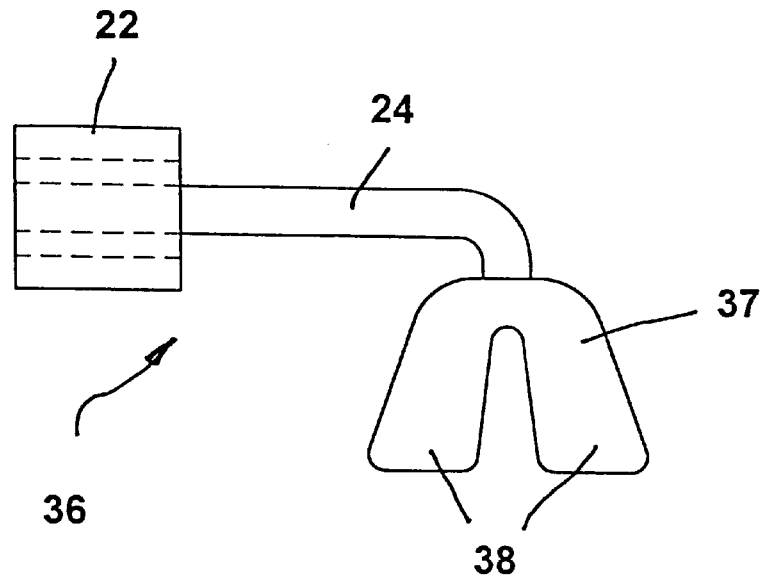
FIGS. 9 and 10 are, respectively, a side view and a back view of a coupling element with a bell-shaped coupling part.
Figure 10:
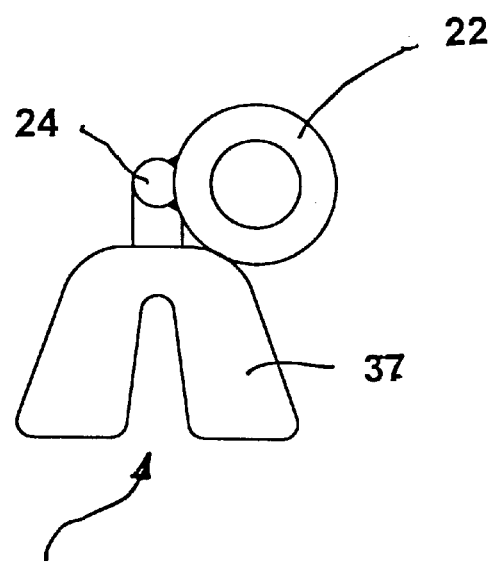

FIGS. 9 and 10 show a further modified coupling element 36 which is suited primarily for coupling to the stapes head when the incus is missing. Coupling element 36 differs from the coupling element 17 of FIGS. 2 through 5 essentially in that, in place of C-shaped coupling part 23, a roughly bell-shaped coupling part 37 is attached to middle part 24. Coupling part 37 can correspond to the convention gold bell of conventional gold wire BELL prostheses (see Steinbach, E.; Pusalkar, A. G.; Plester, D. (1990): Auditory ossicular replacement by gold prostheses. Zentralblatt HNO-Heilkunde 139: 133). Coupling part 37 can be placed on the stapes head and fixed there by pressing bell parts 38 together.

Figure 11:
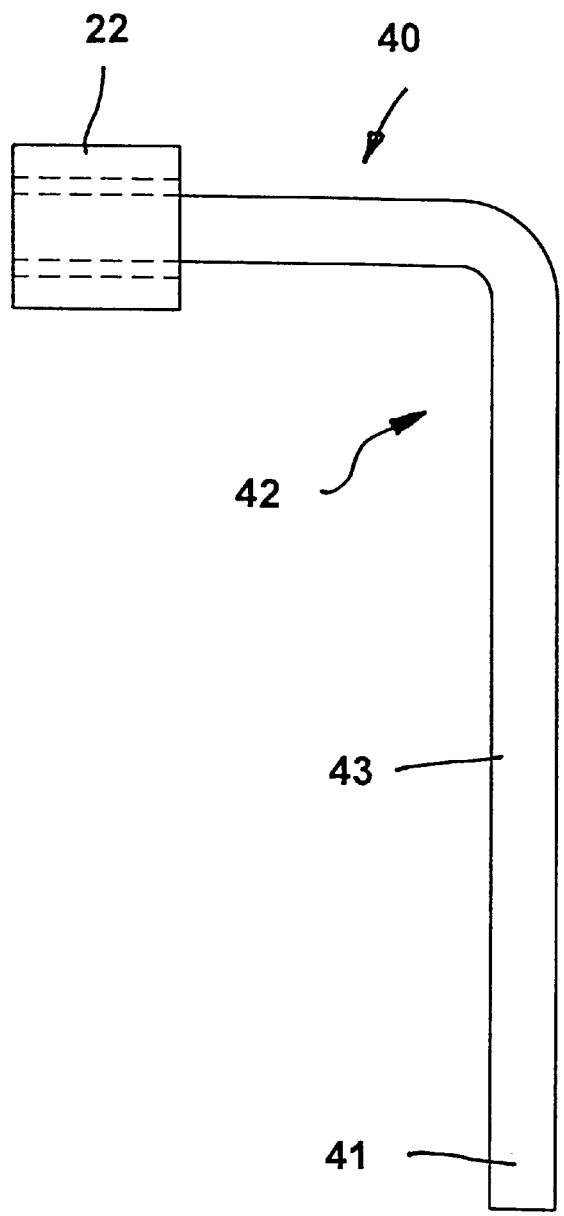
FIGS. 11 and 12 are, respectively, a side view and a back view of a coupling element with a piston-shaped coupling part.
Figure 12:
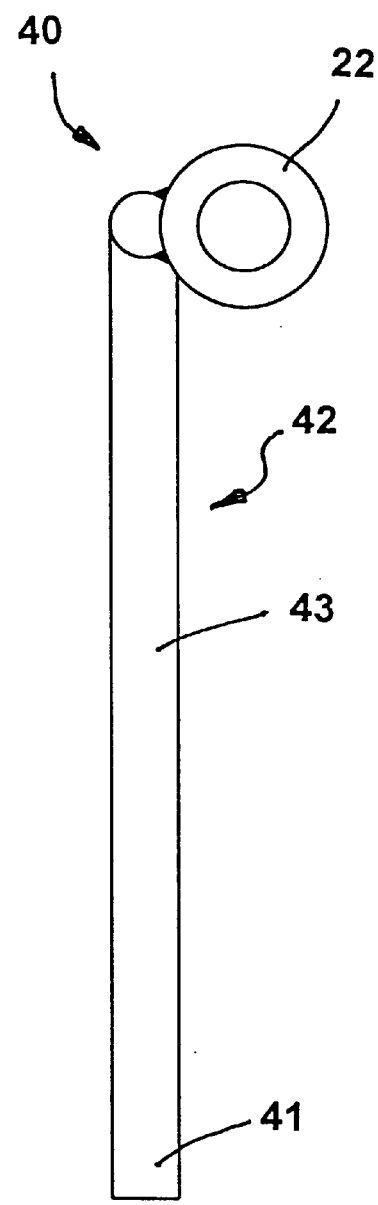

When the stapes superstructure is missing, the coupling of the hearing aid transducer 10 to the perilymph can be produced by means of a coupling element 40 of the type ilustrated in FIGS. 11 and 12. Here, a rod-shaped coupling part 41 is provided in the manner of a stapes-piston prosthesis which is securely joined via an angled middle part 42 to crimp sleeve 22 and represents an integral extension of arm 43 of middle part 42 away from crimp sleeve 22. For purposes of coupling to the perilymph, coupling rod 13 can be guided into the middle ear as an "artificial incus" through an opening of the facial recess (posterior tympanotomy) and its distal end can be positioned over the oval niche. After perforation of footplate 20, for example, by means of an erbium-YAG laser, coupling element 40 is adjusted as in a stapedotomy and attached to coupling rod 13. The coupling part 41 is then inserted into the vestibulum via the footplate perforation.

The aforementioned coupling parts are similar to those of proven standard elements of middle ear prostheses and they offer the advantage that they can be mechanically closed with conventional standard OP instruments, for example, McGee instrument, otosurgical pincers, angulated hook, but, if necessary, can also be opened again.

It is common to the above described embodiments that the crimp sleeve 22 can be loosely placed intraoperatively on the distal end of coupling rod 13, the coupling element pushed or turned axially and radially into the suitable position and the sleeve then crimped securely in situ onto the coupling rod 13.

Basically, external crimping on the operating table is also considered. Generally, however, this is prohibited because the coupling element, of course, can be attached only towards the end of implantation of the hearing aid on the ossicle since, otherwise, an increased risk of inner ear damage would have to be tolerated. Moreover, in external crimping, there is the danger of damaging the coupling element when the coupling rod is inserted. The coupling element could be detached again from the coupling rod then only with considerable cost.

For crimping in situ, especially, a known malleus head disector (for example, STORZ 222800) is suitable; it has been modified in the manner shown in FIGS. 13 through 15 in the cutting area. The crimping tool matched to this object has a stationary part 46 and a part 47 which can be moved with respect to the stationary part. Crimping tool parts 46 and 47 are equipped with arc-shaped blades 48 and 49 which are opposite one another, their radius of curvature being matched to the radius of crimp sleeve 22, preferably the radius of curvature of the blades being somewhat greater than the outside radius of the crimp sleeve.

To attach crimp sleeve 22, blade 48 of the stationary crimping tool part 46 can be placed against crimp sleeve 22 which has been moved into the desired position according to FIGS. 13a and 13b. Then, the blade 49 is moved forward in the direction of arrow 50 onto blade 48 of stationary crimping tool part 46 by pushing crimping tool part 47. Application of a corresponding crimping force deforms, by cold-flow, the crimp sleeve 22 by means of blades 48, 49 in the area of two diametrically opposite, arc-shaped crimping zones 51, 52 which extend in the peripheral direction of crimp sleeve 22 (FIGS. 14a & 14b). Then, by moving the crimping tool part 47 in the direction of arrow 53, the blade 49 is moved away from blade 48 (FIGS. 15a and 15b), whereupon crimping tool 45 is moved out of the middle ear region.

In the explained crimping process, a crimp angle of $\alpha$ (FIG. 13a) of roughly 90 degrees is preferably used. Crimp angle $\alpha$ corresponds intraoperative to the angle between the external auditory canal through which crimping tool 45 is inserted enaurally into the middle ear, and the longitudinal axis of coupling rod 13. In practice, it can happen that coupling rod 13 can only be reached roughly obliquely with the crimping tool 45, but not reliably at a right angle. The blade area of the crimping tool 45 is therefore made preferably such that oblique crimping in the angular range $\alpha=90\pm15$ degrees succeeds. Preferably, the crimping tool 45 is also provided with a mechanical overload protection (not shown by itself) to prevent overly large operating forces.

For permanent and play-free attachment of the crimp sleeve 22 on the coupling rod 13, it is important that the crimp sleeve can be plastically cold-deformed by means of the crimping tool (especially crimping tool 45), and that the coupling rod 13 has a rough surface, at least in the fixing region, and under the influence of the crimping force which is exerted by the crimping tool, that the rod 13 cannot be plastically cold-deformed. It is especially effective if the averaged peak-to-valley height of the surface roughness of coupling rod 13 in the area of the connection to crimp sleeve 22 is at least 10 microns.

Crimp sleeve 22 is preferably made of gold, especially fine gold with a gold content >99.99%, which is preferably soft annealed. The soft annealing can be done, preferably, over roughly 10 minutes at a temperature on the order of 500° C. This soft annealed fine gold can have a Vickers hardness HV of, for example, 30. The high pressing forces applied on both sides by means of blades 48, 49 press a partial area of the crimp sleeve 22 into the rough surface of coupling rod 13. After crimping, sleeve 22 remains plastically deformed, i.e. it no longer springs back into its original position, as is illustrated especially in FIG. 15a. In the area of the force application zones, microdenticulation takes place in this way between crimp sleeve 22 and coupling rod 13. This microdenticulation together with the addition friction force component leads to transferable axial forces in the range of, for example, at least roughly 10 N. These forces are orders of magnitude higher than the necessary stimulation forces.

For the hearing implant, as small a number as possible of different biometals should be used to preclude or minimize undesirable potential formation according to the electrochemical series. Therefore, preferably, not only crimp sleeve 22, but the entire coupling element 17, 29, 36 or 40 (with the exception of C-shaped coupling part 23) desirably should be made of fine gold. For this material, the biocompatibility and long-term stability have been sufficiently verified, especially for the middle ear cavity. In addition, there is post-operative detachability of the ossicle coupling even after years in the body. This detachment of the connection is possible with moderate application of force using standard otosurgical instruments. Connection of coupling element 17, 19, 36, 40 to the respective target ossicle or perilymph can thus take place based on proven standard elements of ordinary passive middle ear prostheses.

However, it goes without saying that, for the coupling element and especially also crimp sleeve 22, other materials are likewise possible. For example, platinum, especially pure platinum, or silver, or alloys of gold, platinum or silver can be used.

Also, implantable titanium, especially pure titanium with a purity of >99.6% is suitable for coupling rod 13. In addition, platinum, niobium, or tantalum or alloys of titanium, platinum, niobium or tantalum are usable. Optionally, the coupling rod 13 can also be made of an implantable ceramic material, especially aluminum oxide.

In the material selection or construction, it should be noted that it is critical to apply the vibratory stimulus (action) of transducer 10 with as little loss as possible to the target ossicle or the perilymph. In doing so, the total mass of the coupling element should preferably be less than the mass of the incus, which is, on average, 25 mg.

Minimization of the weight of the coupling elements, at the same time, leads to reduction of the forces of inertia during acceleration by external effects such as impact, vibration, etc.

The cold flow connection explained in particular above, can also be provided for elements of a passive hearing implant which is made as a total or partial replacement for the ossicular chain. One embodiment for a total prosthesis is shown schematically in FIG. 16 at 58, while FIG. 17 shows an example of a partial prosthesis 59 via a similar schematic representation.

Total prosthesis 58 has a connection element 61 with an eardrum-side coupling part 62 for coupling of the prosthesis to the eardrum and a hollow cylinder part 63 attached securely thereto. On its end away from coupling part 62, the cylinder part 63 passes into the crimp sleeve 22. Furthermore, implant 58 includes a coupling rod 64 which plugs into the crimp sleeve 22 and optionally cylinder part 63. Coupling rod 64, at least in the fixing region, is provided with a rough surface in the manner explained above for coupling rod 13, and in the embodiment shown, it passes in one piece into the rod-shaped coupling part 41 which inserts, via an opening of stapes footplate 20, into the perilymph. Coupling part 41 bears, on its end away from crimp sleeve 22, a stop 65 which is, for example, ring-shaped for limiting the insertion depth of coupling part 41.

Figure 16:
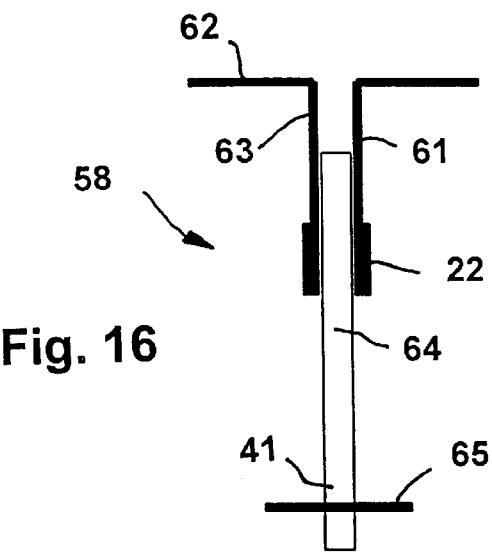
FIG. 16 shows a passive total prosthesis with mutual crimp connection of the two prosthesis parts in schematic form.
Figure 17:
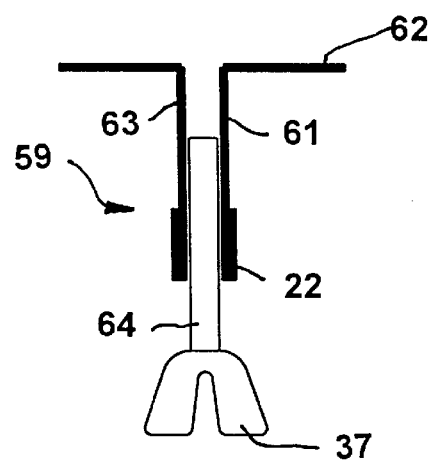
FIG. 17 shows another passive partial prosthesis with mutual crimp connection of the two prosthesis parts.

The partial prosthesis as shown in FIG. 17 differs from the total prosthesis of FIG. 16 essentially only in that the end of coupling rod 64 away from coupling part 62 is joined to a bell-shaped coupling part 37 which can be placed on the stapes head, as described above.

In the implantation of prostheses 58 and 59, connection element 61 and coupling rod 64, analogously to the manner explained above, can be turned to opposite sides and can move in the axial direction, and they can be joined to one another permanently without play by crimping. In this way, the length of the total or partial prosthesis, and if necessary the mutual angular alignment of coupling parts 62 and 41 or 37, can be easily and quickly adjusted intraoperatively according to the individual patient.

Figure 18:
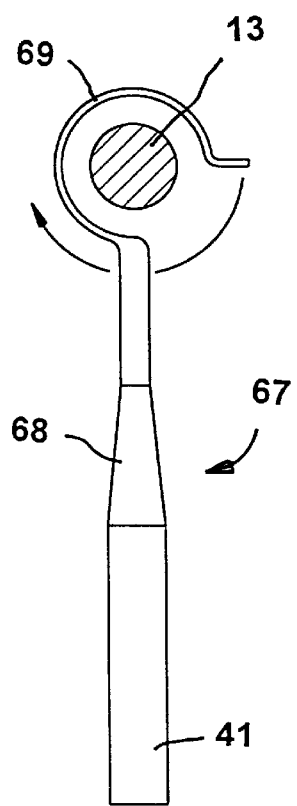
FIG. 18 shows a modified embodiment of an arrangement for adjustment of the relative position of two elements of a hearing aid implant and for fixing these elements in the adjusted relative position with the belt loop not yet tightened.
Figure 19:
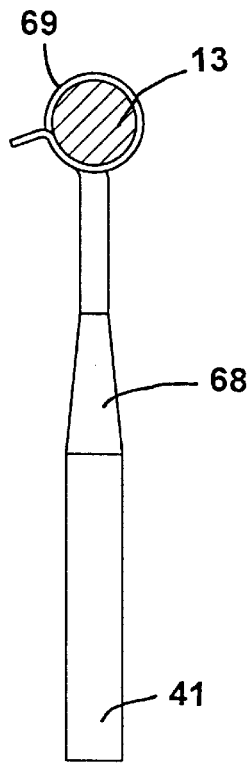
FIGS. 19 and 20 are, respectively, a front view and a side view of the arrangement as shown in FIG. 18 after tightening of the belt loop.
Figure 20:
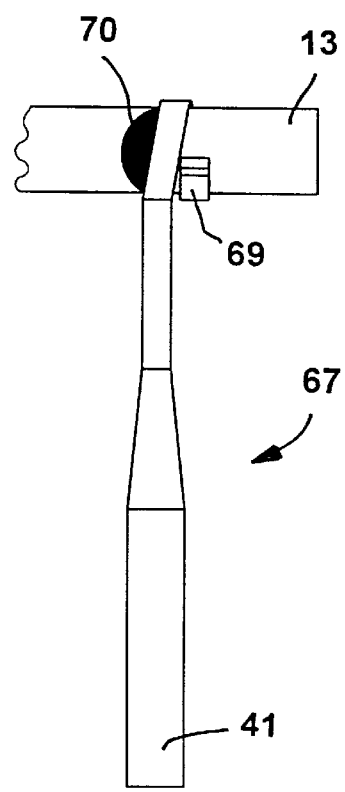

FIGS. 18, 19, and 20 show a further modified embodiment of an arrangement for adjusting the relative position of two elements of a hearing implant and for fixing these elements in the adjusted relative position. Coupling element 67 has rod-shaped coupling part 41 and a belt loop 69 which is joined thereto via intermediate member 68 and which can be tightened around coupling rod 13. In the fixed state illustrated in FIGS. 19 and 20, belt loop 69 loops fully around coupling rod 13, i.e., over an angle of at least 360°, to provide a force-fit and/or form-fit fixing of the belt loop 69 relative to coupling rod 13 in the adjusted position. A form-fit can be provided especially by the fact that not only coupling rod 13, but also belt loop 69, is roughened on its side facing the coupling rod, so that when belt loop 69 is tightened, mutual microdenticulation occurs between the belt loop and coupling rod. Optionally, additional security by material-fit can be provided, for example, by applying a small amount of surgical bone cement 70 in the manner shown schematically in FIG. 20.

It goes without saying that, in the embodiments shown in FIGS. 11, 12 and 18 to 20, in place of a rod-shaped coupling part 41, also a C-shaped coupling part 23 or belt loop 34 or bell-shaped coupling part 37 can be provided. Correspondingly, in the partial prosthesis as shown in FIG. 17, a bell-shaped coupling part 37 can be replaced by a C-shaped coupling part 23 or belt loop 34. Also, with respect to other features, the described arrangements can be easily varied. For example, by means of crimping tool 45, two or more crimp zones can be formed next to one another in successive crimping processes, or the crimping tool can be equipped with two or more blade pairs next to one another. Among others, it is also possible to replace one of two blades 48, 49 by an incus-like counterpiece and to form only one of crimp zones 51 and 52.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. Arrangement for positionally adjusting two elements of a hearing implant relative to each other and for fixing the elements in an adjusted position; wherein at least a part of a first one of the elements in a fixing region thereof being sleeve-shaped and being plastically cold-deformable by a crimping force applied by means of a crimping tool; wherein at least a part of a second one of the elements in a fixing region thereof is rod-shaped, being provided with a rough surface and being resistant to being plastically cold-deformed by the crimping force applied by means of the crimping tool; and wherein, in a fixed state of said parts relative to each other, the sleeve-shaped part of the first one of the elements is permanently attached on the rod-shaped part of the second one of the elements without play by having been cold flow deformed by the crimping force.

2. Arrangement as claimed in claim 1, wherein a crimp angle of the sleeve-shaped part relative to a longitudinal axis of the rod-shaped part is 90°±15°.

3. Arrangement as claimed in claim 2, wherein there are two diametrically opposite crimp zones in the sleeve-shaped part.

4. Arrangement as claimed in claim 3, wherein the crimp zones are arc-shaped and extend in a peripheral direction of the sleeve-shaped part.

5. Arrangement as claimed in claim 1, wherein the surface roughness of the rod-shaped part has an averaged peak-to-valley height of at least 10 microns.

6. Arrangement as claimed in claim 1, wherein there are two diametrically opposite crimp zones in the sleeve-shaped part.

7. Arrangement as claimed in claim 6, wherein the crimp zones are arc-shaped and extend in a peripheral direction of the sleeve-shaped part.

8. Arrangement as claimed claim 1, wherein the first one of the two elements is a coupling rod which is joined with an actively oscillatory part of an implantable hearing aid transducer and the second of the two elements is a coupling element which is connectable to one ossicle of the ossicular chain and perilymph.

9. Arrangement as claimed in claim 8, wherein the coupling element has a crimp sleeve, a coupling part for a respective coupling site in the middle ear and a middle part which connects the crimp sleeve and the coupling part together.

10. Arrangement as claimed in claim 9, wherein the middle part is deformable.

11. Arrangement as claimed in claim 8, wherein the coupling element has a C-shaped coupling part which is positionable around a part of the ossicular chain.

12. Arrangement as claimed in claim 8, wherein the coupling element has a belt loop which is positionable around a part of the ossicular chain.

13. Arrangement as claimed in claim 8, wherein the coupling element has a roughly bell-shaped coupling part which is positionable around a part of the ossicular chain.

14. Arrangement as claimed in claim 8, wherein the coupling element has a rod-shaped coupling part which is insertable into the vestibulum via a stapes footplate perforation.

15. Arrangement as claimed in claim 1, wherein the implant is at least a partial replacement for the ossicular chain.

16. Arrangement as claimed in claim 1, wherein the first one of the elements, at least in the fixing region, is made of a material selected from the group consisting of gold, platinum, silver, or alloys thereof.

17. Arrangement as claimed in claim 16, wherein the second one of the elements, at least in the fixing region, is made of a material selected from the group consisting of titanium, platinum, niobium, or tantalum or alloys thereof, implantable high quality steel, or a ceramic material.

18. Arrangement for adjusting the relative position of two elements of a hearing implant and for fixing the elements in an adjusted position thereof; wherein at least a part of a first one of the elements is belt loop-shaped in a fixing region thereof; wherein at least a part of a second one of the elements is straight rod-shaped in a fixing region thereof; and wherein, in a fixed state of said parts relative to each other, the loop-shaped part extends around the straight rod-shaped part of the second element over an angle of at least 360° and is permanently attached on the rod-shaped part without play by at least one of a force-fit and form-fit type connection.

19. Arrangement as claimed in claim 18, wherein in the fixed state of loop-shaped part, additional securement of the loop-shaped part on the rod-shaped part is provided with a surgical bone cement or glue.

20. Arrangement as claimed in claim 18, wherein the loop-shaped part and the rod-shaped part are roughened on facing surfaces thereof, at least in the fixing region.

21. Arrangement as claimed in claim 18, wherein the loop-shaped part is axially movable along the rod-shaped part prior to fixing thereof.

22. Arrangement as claimed in claim 21, wherein loop-shaped part rotatable relative to the rod-shaped part prior to fixing thereof.

23. Arrangement as claimed in claim 18, wherein the rod-shaped part of other element is straight, at least in the fixing region.

24. Arrangement as claimed in claim 18, wherein the first one of the two elements is a coupling rod which is joined with an actively oscillatory part of an implantable hearing aid tranducer and the second of the two elements is a coupling element which is connectable to one ossicle of the ossicular chain and perilymph.

25. Arrangement as claimed in claim 24, wherein the coupling element has a crimp sleeve, a coupling part for a respective coupling site in the middle ear and a middle part which connects the crimp sleeve and the coupling part together.

26. Arrangement as claimed in claim 25, wherein the middle part is deformable.

27. Arrangement as claimed in claim 24, wherein the coupling element has a C-shaped coupling part which is positionable around a part of the ossicular chain.

28. Arrangement as claimed in claim 24, wherein the coupling element has a belt loop which is positionable around a part of the ossicular chain.

29. Arrangement as claimed in claim 24, wherein the coupling element has a roughly bell-shaped coupling part which is positionable around a part of the ossicular chain.

30. Arrangement as claimed in claim 24, wherein the coupling element has a rod-shaped coupling part which is insertable into the vestibulum via a footplate perforation.

31. Arrangement as claimed in claim 18, wherein the implant is at least a partial replacement for the ossicular chain.

32. Arrangement as claimed in claim 18, wherein the first one of the elements, at least in the fixing region, is made of a material selected from the group consisting of gold, platinum, silver, or alloys thereof.

33. Arrangement as claimed in claim 32, wherein the second one of the elements, at least in the fixing region, is made of a material selected from the group consisting of titanium, platinum, niobium, or tantalum or alloys thereof, implantable high quality steel, or a ceramic material.

* * * * *